United States Patent [19]
Kamiunten

[11] Patent Number: 5,377,527
[45] Date of Patent: Jan. 3, 1995

[54] THERMAL CONDUCTIVITY MEASURING DEVICE

[75] Inventor: Shoji Kamiunten, Kanagawa, Japan

[73] Assignee: Yamatake-Honeywell Co., Ltd., Tokyo, Japan

[21] Appl. No.: 116,866

[22] Filed: Sep. 3, 1993

[30] Foreign Application Priority Data

Sep. 14, 1992 [JP] Japan .................. 4-269131

[51] Int. Cl.$^6$ .................................. G01N 27/18
[52] U.S. Cl. .................................. 73/25.03
[58] Field of Search .................................. 73/25.03

[56] References Cited

U.S. PATENT DOCUMENTS 4,471,647  9/1984  Jerman et al.
4,902,138  2/1990  Goeldner et al. .................. 73/25.03 X Primary Examiner—Hezron E. Williams
Assistant Examiner—Joseph W. Roskos
Attorney, Agent, or Firm—Blakely, Sokoloff, Taylor & Zafman

[57] ABSTRACT

The area of a cross-section perpendicular to a flow direction in a flow path for guiding a sample gas to a detector is set to be larger than that of a cross-section perpendicular to the flow direction in a hollow portion of a base under a membrane of the detector so as to set the volume of the flow path near the hollow portion to be larger than that of the hollow portion. One or both of a thermal conductivity of the gas and its change are measured with high sensitivity and high precision.

4 Claims, 3 Drawing Sheets

THERMAL CONDUCTIVITY MEASURING DEVICE

BACKGROUND OF THE INVENTION

The present invention relates to a thermal conductivity measuring device suitably used in an apparatus such as a gas chromatograph for analyzing the components of a gas to be measured.

As a thermal conductivity measuring device in a gas chromatograph, a filament or a thermister is generally used. As an example of the thermal conductivity measuring device using a thin film formation technique or a micro-machining technique, the device proposed by John H. Jerman et al. (U.S. Pat. No. 4,471,647) is known.

A thermal conductivity measuring device 1 is constituted by a detector 2 and a flow path 3 in which the detector 2 is arranged, as shown in FIGS. 5A, 5B, and 5C. The detector 2 includes a base 5 having a hole 4 in its center and consisting of, e.g., silicon, and a membrane 6 covering one end of the hole 4. The membrane 6 includes elongated metal film resistors 7 located above the hole 4 and constituting a heating member, and a plurality of holes 8 formed such that a gas to be measured (sample gas) flows on both sides of the membrane 6. The detector 2 is placed upside-down above a groove formed in the upper surface of a silicon wafer 9 with the membrane 6 being located at a lower position. A small gap between the membrane 6 and the groove formed in the upper surface of the silicon wafer 9 constitutes the flow path 3. Through holes $15_1$ and $15_2$ connecting the lower surface of the silicon wafer 9 to the flow path 3 are formed on both ends of the flow path 3. In addition, the through holes $15_1$ and $15_2$ are connected to a flow path (not shown) similar to a flow path 17 formed by a glass plate 10 and a groove 16 formed in the lower surface of the silicon wafer 9 to be vertical to the surface of the drawing. The sample gas guided into the flow path 3 through the through hole (e.g., $15_1$) on the upstream side flows along the flow path 3 from right to left and is discharged through the through hole $15_2$ on the downstream side. Note that reference numeral 11 denotes a ring disposed on the silicon wafer 9 to house the base 5; 12, a lid placed on the ring 11; and 13, a gasket disposed between the lid 12 and the base 5.

The thermal conductivity of the sample gas is measured as follows. First, a constant current is supplied to a heating element 7 embedded in the membrane 6 or disposed thereon to generate heat. Then, the quantity of heat dissipated from the heating element 7 changes depending on the thermal conductivity of a gas with which the heating member 7 is brought into contact. This change appears as a change in resistance of the heating element 7, i.e., a change in voltage across the heating element 7. Therefore, the thermal conductivity of the gas can be measured from the value of this change.

In the conventional thermal conductivity measuring device having the above-described structure, the detector itself is used as a constituent element of the flow path 3, and the flow path 3 for guiding a sample gas to the detector 2 is integrally formed with the detector 2. With this structure, in comparison with the volume of a hollow portion 14 formed by the hole 4 of the detector 2 and the membrane 6, the volume of the flow path 3 opposing the hollow portion 14 through the heating element 7 is very small, thus posing the following problems.

When, for example, a gas B which is different from a gas A which has been flowing in the flow path 3 flows to the detector 2 through the flow path 3, the gas A remaining in the hollow portion 14 and the gas B in the flow path 3 near the hollow portion 14 are diffused to each other through the plurality of holes 8 of the membrane 6. Since the volume of the flow path 3 is much smaller than that of the hollow portion 14, and the flow speed is set to be very low to prevent the heating element 7 from being influenced by forced convection, substitution of a gas in the flow path 3 near the hollow portion 14 is very slow to occur. For this reason, the concentration of the gas A in the flow path 3 near the hollow portion 14 is quickly increased, and the concentration gradient of the gas A in the hollow portion 14 and in the flow path 3 is reduced to almost zero. Consequently, diffusion of the gas A from the hollow portion 14 into the flow path 3 near the hollow portion 14 is quickly saturated, resulting in slow progress. In contrast to this, the gas B in the flow path 3 near the hollow portion 14 diffuses into the hollow portion 14. However, since the feed rate of the gas B from the flow path on the upstream side into the flow path 3 near the hollow portion 14 is very low, the concentration gradient of the gas B in the hollow portion 14 and in the flow path 3 near the hollow portion 14 is quickly reduced, and diffusion of the gas B from the flow path 3 near the hollow portion 14 into the hollow portion 14 is quickly saturated, resulting in slow progress. Therefore, the gas A in the hollow portion 14 cannot be smoothly substituted with the gas B, and the gas A also remains in the flow path 3 near the hollow portion 14 in a large quantity, resulting in a large error in measurement of the gas B owing to the residual gas A.

In the use of the device for a gas chromatograph, when a sample gas carried by a carrier gas flows to the detector 2, the carrier gas remaining in the hollow portion 14 of the detector 2 is not smoothly substituted with the sample gas at a position near the heating element 7. In addition, if the flow path 3 is narrow, the amount of sample gas which can flow in the flow path 3 is small. Consequently, the flow of the sample gas is stopped before the carrier gas remaining in the hollow portion 14 of the detector 2 is substituted with the sample gas, and the sample gas to be measured is further diluted with the carrier gas, causing a large measurement error.

Note that the substitution efficiency may be slightly improved by increasing the flow speed in the narrow flow path 3 or increasing the flow rate. However, the quantity of heat dissipated from the heating element 7 is increased by the flow of a gas (force convection), resulting in a large error in thermal conductivity measurement.

SUMMARY OF THE INVENTION

It is, therefore, a principal object of the present invention to provide a thermal conductivity measuring device capable of performing high-precision measurement within a short period of time.

It is another object of the present invention to provide a thermal conductivity measuring device capable of performing high-sensitivity measurement in addition to the above object.

It is still another object to provide a thermal conductivity measuring device which can improve gas substitution efficiency near a heating element of a detector and can measure one or both of a thermal conductivity and a change in thermal conductivity with high sensitivity and high precision.

In order to achieve the above objects, according to the present invention, there is provided a thermal conductivity measuring device including a detector having a heating element held in the air by a membrane formed above a hollow portion of a base, and a flow path for guiding a gas to be measured to the detector, and designed to measure either or both of a thermal conductivity of the gas and a change in thermal conductivity of the gas, wherein an area of a cross-section perpendicular to a flow direction in the flow path is set to be larger than an area of a cross-section perpendicular to a flow direction in the hollow portion under the membrane of the detector.

As described above, the volume of the flow path near the hollow portion is set to be larger than that of the hollow portion. With this structure, even if the flow speed of a gas is set to be low to prevent the heating element from being influenced by forced convection, a large amount of gas is fed into the flow path near the hollow portion. When, for example, a gas B which is different from a gas A which has been flowing in the flow path flows to the detector through the flow path, the gas A remaining in the hollow portion and the gas B in the flow path near the hollow portion are diffused to each other through the plurality of slits of the membrane. As a result, the gas A in the hollow portion diffuses into the flow path near the hollow portion, whereas the gas B in the flow path near the hollow portion diffuses into the hollow portion. Since the concentration of the gas A in the flow path near the hollow portion is kept lower than that in the hollow portion until the gas A near the membrane is completely substituted with the gas B, diffusion of the gas A from the hollow portion into the flow path near the hollow portion can be efficiently performed to the end. Meanwhile, diffusion of the gas B from the flow path near the hollow portion into the hollow portion can be efficiently performed to the end because the concentration of the gas B in the flow path near the hollow portion is kept higher than that in the hollow portion.

DESCRIPTION OF THE PREFERRED EMBODIMENTS

The present invention will be described in detail below with reference to the embodiments shown in the accompanying drawings.

Figure 1A:
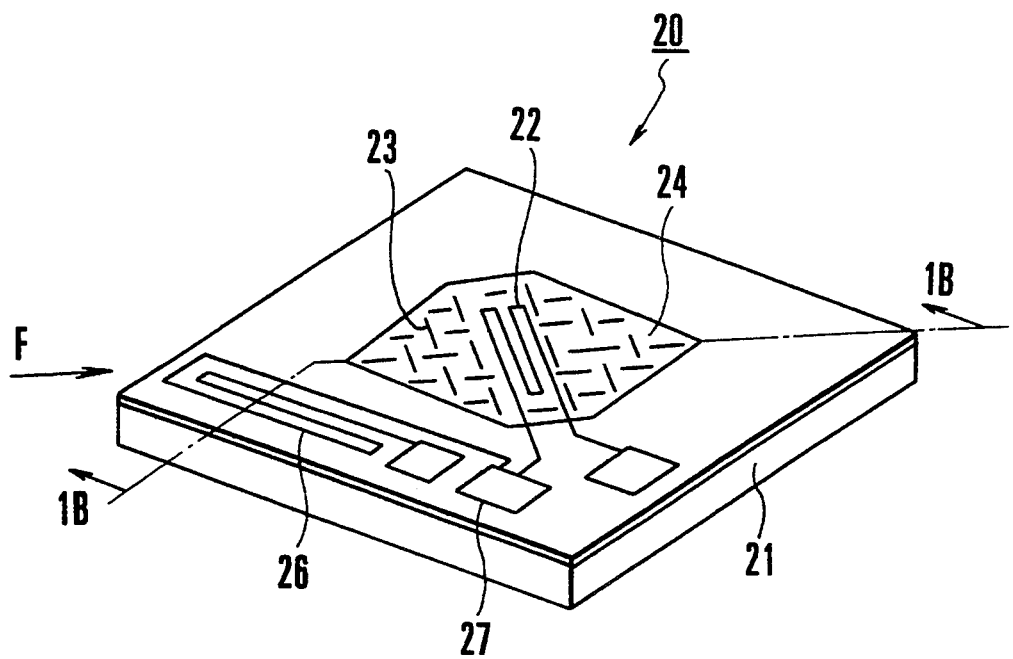
FIGS. 1A and 1B are a perspective view and a sectional view, respectively, showing a detector in a thermal conductivity measuring device according to an embodiment of the present invention.
Figure 1B:
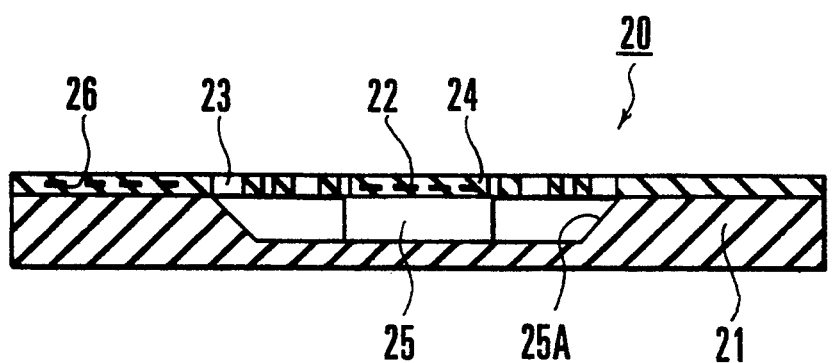
Figure 2A:
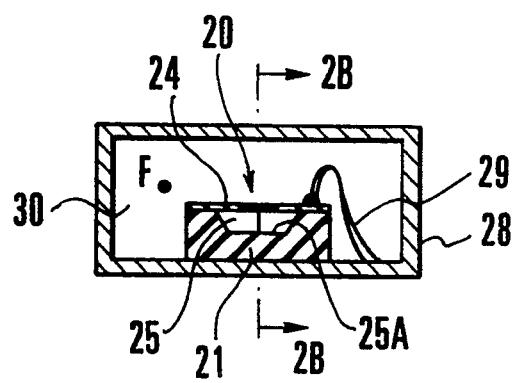
FIGS. 2A and 2B are sectional views taken along directions perpendicular and parallel to the flow of a gas, respectively, showing the arrangement of the detector and a flow path.
Figure 2B:
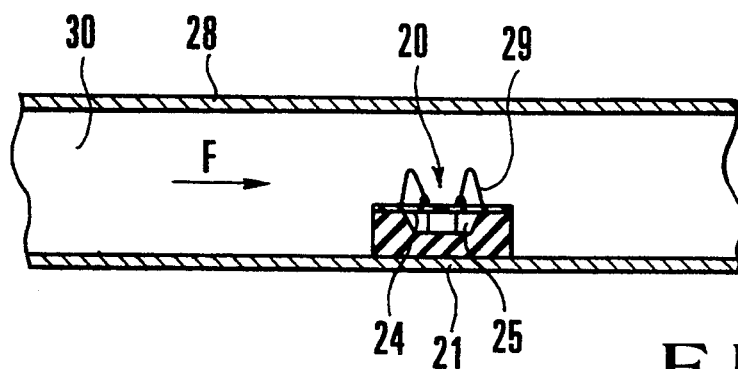

FIGS. 1A and 1B show a detector as an embodiment of the present invention, which detector is formed by a micro-machining technique such as anisotropic etching and a thin film formation technique. FIGS. 2A and 2B show the relationship between the detector and a flow path.

Referring to FIGS. 1A to 2B, reference numeral 20 denotes a detector; and 21, a base consisting of, e.g., a silicon material. A recess portion 25A defining a hollow portion 25 is formed in a central portion of the upper surface of the base 21. A membrane 24 composed of an insulating thin film consisting of $SiO_2$, $Si_3N_4$, or the like is formed on the upper surface of the base 21 to cover the recess portion 25A. A heating element 22 constituted by a resistor pattern consisting of platinum, permalloy, or the like, and a plurality of slits 23 are formed in the membrane 24. An ambient temperature sensor 26 is formed on a portion, of the base 21, in which the recess portion 25A is not formed. Ambient temperature correction can be performed by using the sensor 26. In this embodiment, the heating element 22 and the sensor 26 are embedded in the membrane 24.

The detector 20 having the above-described structure is placed in a flow path 30 and constitutes the thermal conductivity measuring device together with the flow path 30. Note that reference numeral 27 denotes electrode pads; 28, a pipe constituting the flow path 30; and 29, gold wires. In this case, the heating element 22 extends from the pads 27 of the base 21 to the membrane 24 above the recess portion 25A. On the membrane 24, the heating element 22 is disposed with its wire material being bend in the form of a comb. In this case, in order to increase the measurement precision and shorten the measuring time, the heating element 22 is generally arranged such that its longitudinal direction is perpendicular to the flow direction (indicated by an arrow F) in the flow path, as shown in FIG. 1A. However, is should be noted that the arrangement of the heating element 22 is not limited to such a positional relationship.

Consider the device in terms of dimension. For example, a cross-section of the flow path 30 has a height of 1 mm and a width of 4 mm; a cross-section of the hollow portion 25 between the membrane 24 of the detector 20 and the recess portion 25A of the base 21 has a height of 0.2 mm and a maximum width of 0.6 mm; and a cross-section of the base 21 has a height of 0.4 mm and a maximum width of about 2.4 mm. That is, the area of a cross-section perpendicular to the flow direction (indicated by the arrow F) in the flow path 30 is set to be larger than that of a cross-section perpendicular to the flow direction in the hollow portion 25 between the membrane 24 of the detector 20 and the recess portion 25A of the base 21.

As described above, since the area of the cross-section perpendicular to the flow direction in the flow path 30 is set to be larger than that of the cross-section perpendicular to the flow direction in the hollow portion 25 of the detector 20, the volume of the flow path 30 near the hollow portion 25 is larger than that of the hollow portion 25. For this reason, even if the flow speed of a gas is set to be low to prevent the heating element 22 from being influenced by forced convection, the amount of gas fed into the flow path 30 is large. When, for example, a gas B which is different from a gas A which has been flowing in the flow path 30 flows to the detector 20 through the flow path 30, the gas A remaining in the hollow portion 25 and the gas B in the flow path 30 near the hollow portion 25 are diffused to each other through the plurality of slits 23 of the membrane 24. As a result, the gas A in the hollow portion 25 diffuses into the flow path 30 near the hollow portion 25, whereas the gas B in the flow path 30 near the hollow portion 25 diffuses into the hollow portion 25. However, the concentration of the gas A in the flow path 30 near the hollow portion 25 is kept lower than that in the hollow portion 25 until the gas A near the membrane 24 is completely substituted with the gas B. Therefore, diffusion of the gas A from the hollow portion 25 into the flow path 30 near the hollow portion 25 can be efficiently performed to the end. Meanwhile, diffusion of the gas B from the flow path 30 near the hollow portion 25 into the hollow portion 25 can be efficiently performed to the end because the concentration of the gas B in the flow path 30 near the hollow portion 25 is kept higher than that in the flow path 30. Consequently, substitution of a gas near the heating element 22 of the detector 20 can be smoothly performed.

In the use of the device for a gas chromatograph, when a sample gas carried by a carrier gas flows to the detector 20, the carrier gas is quickly substituted with the sample gas near the heating element 22. Therefore, high-sensitivity, high-precision gas analysis can be performed at a high speed.

Figure 3:
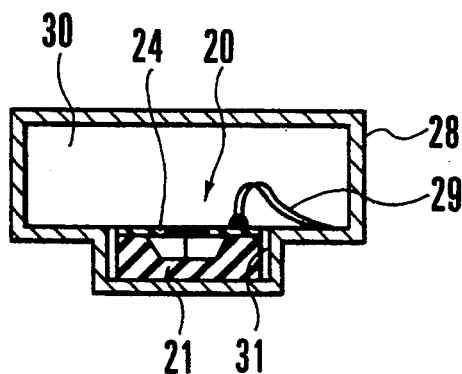
FIG. 3 is a sectional view showing a thermal conductivity measuring device according to another embodiment of the present invention.

The arrangement of the detector 20 and the cross-section perpendicular to the flow direction in the flow path 30 is not limited to that shown in FIG. 2A. For example, as shown in FIG. 3, a detector 21 may be inserted in a recess portion 31 formed in the inner lower surface of a pipe 28, and the upper surface of the base 21 may be set at almost the same level as that of the inner lower surface of the pipe 28. In this structure, the upper surface of the base 21 is in contact with the flow of a gas in the flow path.

Figure 4:
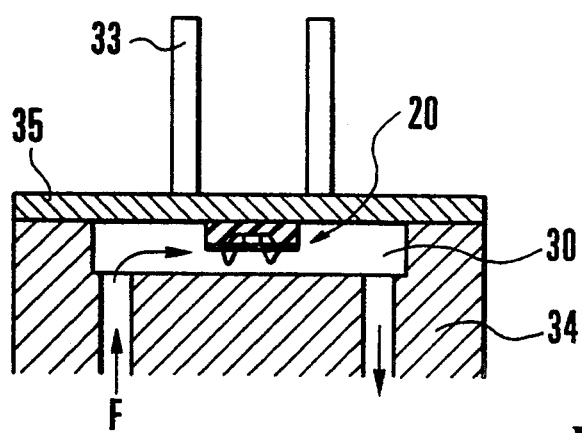
FIG. 4 is a sectional view taken along a direction parallel to the flow of a gas, showing the detailed structure of a detector and a flow path according to still another embodiment of the present invention.

FIG. 4 shows the detailed structure of a detector 20 and a flow path 30 according to still another embodiment of the present invention. Reference numeral 33 denotes lead pins; 34, a flow path block; and 35, a ceramic substrate.

Figure 5A:
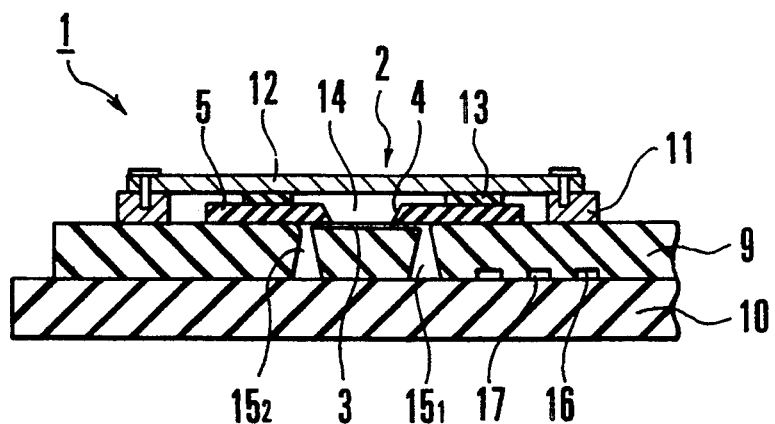
FIGS. 5A, 5B, and 5C are sectional views and an enlarged sectional view of a main part, respectively, showing a conventional thermal conductivity measuring device.
Figure 5B:
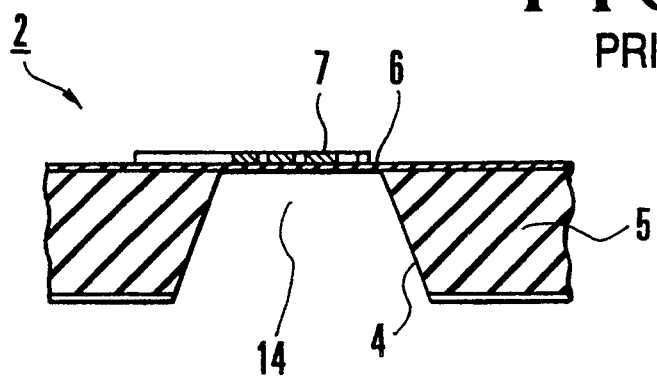
Figure 5C:
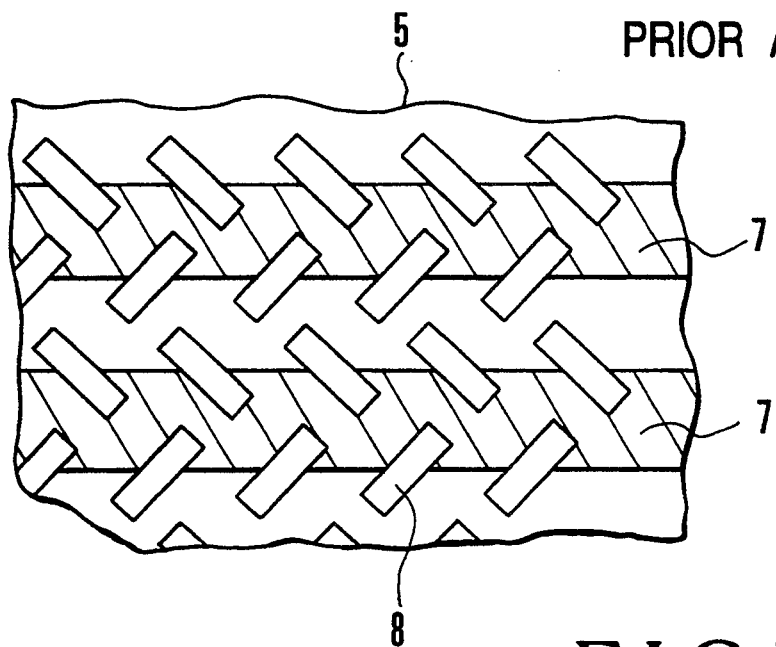

In the thermal conductivity measuring device (shown in FIGS. 5A to 5C) proposed by John H. Jerman et al. (U.S. Pat. No. 4,471,647), the membrane 6 having the plurality of holes 8 is formed by etching the base 5 from its lower surface side. For this reason, the volume of the hollow portion 14 becomes unnecessarily large to hinder quick substitution of a gas in the hollow portion 14 and increase the base 5 in size, posing various problems. For example, the mechanical strength of the base 5 is low, and positioning is required on both the upper and lower surface sides of the base 5 in the manufacturing process. In addition, the opening in the lower surface of the base 5 adversely affects packaging. In contrast to this, In the detector 20 shown in FIG. 1 according to the present invention, anisotropic etching of the base 21 under the membrane 24 is performed, from the upper surface side of the base 21, through the plurality of slits 23 formed in the membrane 24 to form the structure in which the membrane 24 is floating in the air in the hollow portion 25. With this structure, the device has the following excellent characteristics.

Since the volume of the hollow portion 25 can be limited to the minimum value required for heat insulation between the heating portion and the base 21, substitution of a gas in the hollow portion 25 can be quickly performed. In addition, the size of the base 21, can be reduced, and the base 21 has a high mechanical strength. In the manufacturing process, positioning on the upper and lower surface sides of the base 21 need not be performed, and packaging can be easily performed. Of these advantages, especially the advantage that the volume of the hollow portion 25 and the size of the base 21 can be reduced makes the above-described detector optimal as a device used for the present invention, and also allows a reduction in size of the flow path.

In this embodiment, the flow path 30 is formed to have a rectangular cross-section. However, the present invention is not limited to this. For example, the flow path may have a circular cross-section.

The materials for the base 21, the membrane 24, the resistor pattern, and the like constituting the detector 20 are not limited to those described in this specification. For example, it is apparent that a metal plate such as an aluminum or stainless plate may be used as a base, and the membrane 24 may be formed of an insulating film consisting of $SiO_2$, $Si_3N_4$, or the like.

In addition, the resistor pattern is preferably embedded in the membrane 24 or coated with a some kind of protective film after it is formed on the membrane 24. However, the present invention is not limited to this.

The word "membrane" used in the present invention can be expressed by other words such as "diaphragm" and "film".

In the above-described embodiments, the recess portion or the hollow portion 25 is formed by a known etching technique such as anisotropic etching or isotropic etching. Although the membrane 24 can be formed by a known etching technique, it can also be formed by a process technique using an end mill or a laser. Furthermore, the base 21 and the membrane 24 may be formed separately to be joined to each other afterward.

As has been described above, in the thermal conductivity measuring deice according to the present invention, the area of the cross-section perpendicular to the flow direction in the flow path for guiding a sample gas to the detector is set to be larger than that of the cross-section perpendicular to the flow direction in the hollow portion of the base under the membrane of the detector so as to set the volume of the flow path near the hollow portion to be larger than that of the hollow portion. With this structure, even if the flow speed of a gas is set to be low to prevent the heating element from being influenced by forced convection, a large amount of gas is fed into the flow path near the hollow portion. When, for example, a gas B which is different from a gas A which has been flowing in the flow path flows to the detector through the flow path, the gas A remaining in the hollow portion and the gas B in the flow path near the hollow portion are diffused to each other through the plurality of slits of the membrane. As a result, the gas A in the hollow portion diffuses into the flow path near the hollow portion, whereas the gas B in the flow path near the hollow portion diffuses into the hollow portion. Since the concentration of the gas A in the flow path near the hollow portion is kept lower than that in the hollow portion until the gas A near the membrane is completely substituted with the gas B, diffusion of the gas A from the hollow portion into the flow path near the hollow portion can be efficiently performed to the end. Meanwhile, diffusion of the gas B from the flow path near the hollow portion into the hollow portion can be efficiently performed to the end because the concentration of the gas B in the flow path near the hollow portion is kept higher than that in the hollow portion. Therefore, substitution of a sample gas near the heating element of the detector can be smoothly performed, allowing high-sensitivity, high-precision measurement of one or both of a thermal conductivity and a change in thermal conductivity at a high speed. Furthermore, in the use of the device for a gas chromatograph, when a sample gas carried by a carrier gas flows to the detector, the carrier gas is quickly substituted with the sample gas at a position near the heating element, thereby allowing high-speed analysis with high sensitivity and high precision.

What is claimed is:

1. A thermal conductivity measuring device comprising:

a base with a hollow portion;

a membrane formed above said hollow portion of said base;

a detector having a heating element held in the air by said membrane, and wherein said detector measures at least one of the thermal conductivity of a gas and a change in thermal conductivity of a gas; and a flow path for guiding gas to be measured to said detector;

wherein an area of a cross-section perpendicular to the flow direction in said flow path, and over said detector, is set to be larger than an area of a cross section perpendicular to the flow direction in the hollow portion under said membrane of said detector.

2. A device according to claim 1, wherein said detector is housed in a recess portion formed in said flow path, and an upper surface of said detector is in contact with a flow of a gas in said flow path.

3. A device according to claim 1, wherein said heating element is arranged such that a longitudinal direction thereof is perpendicular to the flow direction in said flow path.

4. A device according to claim 1, wherein said detector contacts gas as it is moving through said flow path.

* * * * *